United States Patent
Otsuka et al.

(10) Patent No.: US 8,791,310 B2
(45) Date of Patent: Jul. 29, 2014

(54) PROCESS FOR PRODUCING FLUOROALKYL IODIDE

(71) Applicant: Asahi Glass Company, Limited, Chiyoda-ku (JP)

(72) Inventors: Tetsuo Otsuka, Chiyoda-ku (JP); Shoji Furuta, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 13/693,592

(22) Filed: Dec. 4, 2012

(65) Prior Publication Data

US 2013/0096353 A1 Apr. 18, 2013

Related U.S. Application Data

(63) Continuation of application No. PCT/JP2011/062732, filed on Jun. 2, 2011.

(30) Foreign Application Priority Data

Jun. 4, 2010 (JP) .................................. 2010-129013

(51) Int. Cl.
   - *C07C 17/278* (2006.01)
   - *C07C 17/26* (2006.01)
   - *C07C 17/272* (2006.01)
   - *C07C 17/20* (2006.01)

(52) U.S. Cl.
   CPC .............. *C07C 17/202* (2013.01); *C07C 17/272* (2013.01); *C07C 17/278* (2013.01)
   USPC ............................ 570/171; 570/172; 570/137

(58) Field of Classification Search
   None
   See application file for complete search history.

(56) References Cited

U.S. PATENT DOCUMENTS

| | | | |
|---|---|---|---|
| 3,226,449 A | | 12/1965 | Blanchard et al. |
| 4,049,732 A | * | 9/1977 | Bach et al. ................. 585/320 |
| 2007/0249876 A1 | * | 10/2007 | Furuta et al. ............... 570/171 |

FOREIGN PATENT DOCUMENTS

| | | |
|---|---|---|
| CN | 1854117 A | 11/2006 |
| GB | 1256818 | 3/1970 |
| JP | 48-68508 | 9/1973 |
| JP | 5-255146 | 10/1993 |
| JP | 6-206908 | 7/1994 |

(Continued)

OTHER PUBLICATIONS

Furuta et al. JP2009-073762A (Engllish translation).*

(Continued)

*Primary Examiner* — Jafar Parsa
*Assistant Examiner* — Medhanit Bahta
(74) *Attorney, Agent, or Firm* — Oblon, Spivak, McClelland, Maier & Neustadt, L.L.P.

(57) ABSTRACT

To provide a process for producing a fluoroalkyl iodide, whereby the selectivity for a fluoroalkyl iodide having a desired degree of polymerization is high and the productivity is high. A process for producing a fluoroalkyl iodide (2) represented by $R^f CF_2 CF_2 I$ (wherein $R^f$ is a fluoroalkyl group having at most 4 carbon atoms), which comprises reacting a fluoroalkyl iodide (1) represented by $R^f I$ with tetrafluoroethylene in the presence of a radical initiator, wherein a first reaction step of supplying and reacting tetrafluoroethylene and a radical initiator to the fluoroalkyl iodide (1), is followed by repeating (n−1) times (provided that n is an integer of at least 3) a subsequent reaction step of supplying and reacting a radical initiator, or a radical initiator and tetrafluoroethylene, to a reaction mixture (1) formed in the first reaction step.

18 Claims, 1 Drawing Sheet

(56) References Cited

FOREIGN PATENT DOCUMENTS

| | | |
|---|---|---|
| JP | 6-305995 | 11/1994 |
| JP | 8-239335 | 9/1996 |
| JP | 8-239336 | 9/1996 |
| JP | 02/062735 | 8/2002 |
| JP | 2009-73762 | 4/2009 |
| JP | 2009073762 A * | 4/2009 |
| WO | 02/062735 | 8/2002 |
| WO | 2007/102371 | 9/2007 |
| WO | 2009/034859 | 3/2009 |

OTHER PUBLICATIONS

Chinese Patent Application 2011800271864, Dec. 26, 2014.
U.S. Appl. No. 14/103,072, filed Dec. 11, 2013, Furuta, et al.
International Search Report issued Aug. 9, 2011 in PCT/JP2011/062732 filed Jun. 2, 2011.

* cited by examiner

006# PROCESS FOR PRODUCING FLUOROALKYL IODIDE

TECHNICAL FIELD

The present invention relates to a process for producing a fluoroalkyl iodide by telomerization.

BACKGROUND ART

A fluoroalkyl iodide (hereinafter sometimes referred to as $R^F I$) is useful as a material for synthesis of a fluoroalkyl acrylate constituting a water/oil repellent latex, a material for synthesis of a fluorinated surfactant, etc.

Recently, EPA (US Environmental Protection Agency) has pointed out that a compound having a perfluoroalkyl group having at least 8 carbon atoms (hereinafter, the perfluoroalkyl group may be presented also as a $R^F$ group) is likely to be decomposed in vivo or in the environment, whereupon the decomposition product is likely to be accumulated, i.e. the environmental load tends to be high. Therefore, it is required to reduce the compound having a $R^F$ group having at least 8 carbon atoms as far as possible.

In the fluoroalkyl iodide, the carbon chain length of $R^F$ desired to obtain water/oil repellency is usually C4 or longer, although it may depend also upon the purpose of use. For production of $R^F I$ having such a carbon chain length, chain length elongation by addition of a taxogen employing a short chain $R^F I$ as a telogen i.e. telomerization is utilized. As the taxogen, usually tetrafluoroethylene $CF_2CF_2$ (hereinafter sometimes referred to as TFE) is used, and thus a telomer fluoroalkyl iodide $R^F I$ is obtained as $R^F(CF_2CF_2)_n I$ (n is the degree of polymerization). The starting material telogen $R^F I$ is typically $C_2F_5I$, which is synthesized from tetrafluoroethylene, $IF_5$ and $I_2$.

By simply carrying out the telomerization, a 1:1 addition product of a telogen and a taxogen mainly forms, and only a very small amount of a telomer having a chain length more highly elongated will be obtained. It has been known that the efficiency of formation of C6-12 $R^F I$ will be increased by use of a free radical-generating catalyst such as a peroxide for the telomerization (for example, Patent Document 1). The publication also discloses use of a telogen mixture of $C_2F_5I$ and $C_4F_9I$. The reaction in this publication is a liquid phase reaction conducted in one step.

In addition to the reaction by means of free radical generation, telomerization by a catalytic reaction utilizing the redox system and telomerization by thermal reaction have been known. In order to reduce the compound having at least 8 carbon atoms, formation of a telomer having a narrow distribution in a specific chain length range or a telomer having a single chain length is required to obtain desired characteristics. However, in each of the above methods, selectivity for a single chain length tends to be low, control of the chain length is difficult, and a telomer mixture having a broad chain length distribution will be obtained.

It has been known that in the thermal reaction of reacting a telogen and a taxogen in a vapor phase, the proportion of formation of a long chain telomer exceeding C14 can be reduced by increasing the ratio of telogen/taxogen. In order to reduce the proportion of formation of a long chain telomer in the vapor phase reaction, a continuous process of dividedly supplying the taxogen TFE from an inlet of a tubular reactor and from another portion, has been proposed (for example, Patent Document 2). This publication also discloses that the chain length distribution can be narrowed when telomers having chain lengths of C4 and C6 which are sequentially formed are used as the telogen together with the C2 starting material, as compared with a case where the C2 starting material is used alone as the telogen.

Further, it has been proposed that in the above thermal telomerization in the vapor phase, a telomer having a chain length shorter than the final chain length is recycled to a predetermined zone of the reactor so as to improve the selectivity for the carbon chain length (for example, Patent Document 3).

According to the above vapor phase telomerization, a fluoroalkyl iodide telomer having a relatively narrow chain length distribution can be obtained, but the telomerization has to be carried out under extremely restricted conditions with regard to e.g. introduction of the material taxogen or the recycled telomer to the reactor. Further, due to the vapor phase reaction, there is such a problem that a perfluoroalkyl compound is formed as an impurity by coupling of fluoroalkyl radicals to be generated during the reaction.

On the other hand, a liquid phase reaction employing a catalyst is advantageous in view of energy since the reaction temperature is inherently low as compared with the above vapor phase reaction, and is advantageous in that a thermally unstable taxogen (TFE) is less likely to be decomposed. A process is disclosed wherein the liquid phase reaction is carried out in a slender cylindrical reaction space, the reaction mixture which left the cylindrical reaction space is separated, and a telomer having the reaction progressed is drawn, and on the other hand, a telomer having no desired chain length and an unreacted material are recycled to the initial stage of the reaction system (Patent Document 4). Patent Document 4 discloses that the proportion of formation of C8 and longer telomers can be improved. Further, the waste gas can be reduced by the recycle.

Further, a process by a liquid phase reaction has been proposed which comprises separating the reaction mixture of the initial material telogen and TFE into three fractions, and subjecting a second fraction having a degree of polymerization of TFE lower by 1 than the desired degree of polymerization to reaction in a second reactor (Patent Document 5). In this process, a telomer mixture having at least a desired degree of polymerization is obtained by a two-step reaction. No special reactor is required for each of the two reactors, and the reactor may be an autoclave or the like.

The above telomerization by means of a liquid phase method is advantageous over a vapor phase method in view of operation and energy, and in that no impurities such as a perfluoroalkyl compound will be formed as by-products. By the telomerization by means of a liquid phase method, a telomer having a desired chain length or longer will be obtained, but it tends to be difficult to control the chain length, and particularly it tends to be difficult to suppress formation of a telomer having a chain longer than the desired chain length. Even when a known reaction method is applied so as to control the chain length, a telomer having a broad chain length distribution will be obtained in fact. Further, in continuous operation, a telomer having the chain length controlled will be obtained by removing an unreacted product from the reaction product as far as possible, but such remarkably decreases the reaction efficiency. As mentioned above, it is difficult to obtain a fluoroalkyl iodide telomer having a narrow chain length distribution in a desired range, particularly a fluoroalkyl iodide telomer having an aimed single carbon chain length with high production efficiency, by a telomerization process by means of a liquid phase method.

PRIOR ART DOCUMENTS

Patent Documents

Patent Document 1: U.S. Pat. No. 3,226,449
Patent Document 2: JP-A-5-255146
Patent Document 3: JP-A-6-305995
Patent Document 4: JP-A-6-206908
Patent Document 5: WO02-062735

DISCLOSURE OF INVENTION

Technical Problem

It is an object of the present invention to provide a process for producing a fluoroalkyl iodide, whereby a fluoroalkyl iodide having a small environmental load can be produced selectively and efficiently.

Solution to Problem

The present invention provides a process for producing a fluoroalkyl iodide, which has the following construction.

[1] A process for producing a fluoroalkyl iodide (2) represented by the following formula (2), which comprises reacting a fluoroalkyl iodide (1) represented by the following formula (1) with tetrafluoroethylene in the presence of a radical initiator:

$R^f I$      (1)

$R^f CF_2CF_2I$      (2)

wherein $R^f$ is a fluoroalkyl group having at most 4 carbon atoms, wherein by a first reaction step of supplying and reacting tetrafluoroethylene and a radical initiator to the fluoroalkyl iodide (1), followed by a second reaction step of supplying and reacting a radical initiator, or a radical initiator and tetrafluoroethylene, to a reaction mixture (1) formed in the first reaction step, a reaction mixture (2) comprising the fluoroalkyl iodide (1) and the fluoroalkyl iodide (2) is produced, the maximum amount of tetrafluoroethylene present in each reaction step is maintained to be within a range of from 0.01 to 10 mol % to the total number of moles of the fluoroalkyl iodide (1) and the fluoroalkyl iodide (2), the maximum amount of the radical initiator present in each reaction step is adjusted to be from 0.0005 to 0.5 mol % to the total number of moles of the fluoroalkyl iodide (1) and the fluoroalkyl iodide (2), and the conversion of the fluoroalkyl iodide (1) in the reaction mixture (2) after completion of the second reaction step is adjusted to be at most 10%.

[2] A process for producing a fluoroalkyl iodide (2) represented by the following formula (2), which comprises reacting a fluoroalkyl iodide (1) represented by the following formula (1) with tetrafluoroethylene in the presence of a radical initiator:

$R^f I$      (1)

$R^f CF_2CF_2I$      (2)

wherein $R^f$ is a fluoroalkyl group having at most 4 carbon atoms, wherein by a first reaction step of supplying and reacting tetrafluoroethylene and a radical initiator to the fluoroalkyl iodide (1), followed by a total of n reaction steps by repeating (n−1) times (provided that n is an integer of at least 3) a subsequent reaction step of supplying and reacting a radical initiator, or a radical initiator and tetrafluoroethylene, to a reaction mixture (n−1) formed in the preceding reaction step, a reaction mixture (n) comprising the fluoroalkyl iodide (1) and the fluoroalkyl iodide (2) is produced, the maximum amount of tetrafluoroethylene present in each reaction step is maintained to be within a range of from 0.01 to 10 mol % to the total number of moles of the fluoroalkyl iodide (1) and the fluoroalkyl iodide (2), the maximum amount of the radical initiator present in each reaction step is adjusted to be from 0.0005 to 0.5 mol % to the total number of moles of the fluoroalkyl iodide (1) and the fluoroalkyl iodide (2), and the conversion of the fluoroalkyl iodide (1) in the reaction mixture (n) after completion of the n-th reaction step is adjusted to be at most 10%.

[3] The process according to [1] or [2], which has, prior to each reaction step, a step of mixing the fluoroalkyl iodide (1) and/or the fluoroalkyl iodide (2), tetrafluoroethylene and the radical initiator by a stirrer.

[4] The process according to any one of [1] to [3], which has a step (d) of separating the fluoroalkyl iodide (2) from the reaction mixture (2) or the reaction mixture (n) after completion of the n-th reaction step.

[5] The process according to any one of [1] to [4], wherein the reaction temperature in each reaction step is from 40 to 120° C.

[6] The process according to any one of [1] to [5], wherein after separating the fluoroalkyl iodide (2) from the reaction mixture (2) or the reaction mixture (n), the fluoroalkyl iodide (1) is used as the fluoroalkyl iodide in the reaction step (1).

[7] The process according to any one of [1] to [6], wherein the fluoroalkyl iodide (1) is $C_4F_9I$, or a mixture of $C_4F_9I$ and $C_2F_5I$.

[8] The process according to any one of [1] to [7], wherein the fluoroalkyl iodide (2) is $C_6F_{13}I$.

[9] The process according to any one of [1] to [8], wherein the radical initiator is a fluorinated peroxide.

[10] The process according to any one of [1] to [9], wherein the conversion of the fluoroalkyl iodide (1) is from 1.8 to 5%, and the selectivity for a fluoroalkyl iodide having at least 8 carbon atoms is at most 6%.

Advantageous Effects of Invention

According to the process of the present invention, a fluoroalkyl iodide (2) having a desired degree of polymerization can be produced at a high selectivity and a high productivity.

DESCRIPTION OF EMBODIMENTS

In this specification, a fluoroalkyl iodide (1) will be referred to as a compound (1). Likewise, a fluoroalkyl iodide (2) may be referred to as a compound (2). Further, in this specification, a $R^f$ group is a group having some or all of hydrogen atoms in an alkyl group substituted by fluorine atoms, and a $R^E$ group is a group having all of hydrogen atoms in an alkyl group substituted by fluorine atoms.

Figure 1:
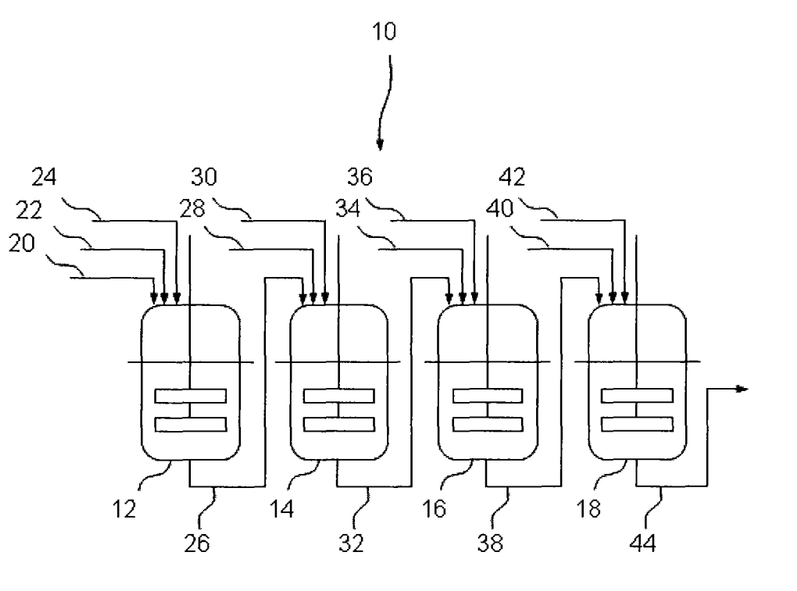
FIG. 1 is a schematic view of an apparatus for producing a fluoroalkyl iodide.

FIG. 1 is a construction view showing an example of the apparatus for producing a fluoroalkyl iodide. A production apparatus 10 comprises a reactor 12 to prepare a mixed solution 1 containing the compound (1), tetrafluoroethylene and a radical initiator and to add tetrafluoroethylene to the compound (1) thereby to obtain a reaction mixture (1) containing the compound (2); a reactor 14 to prepare a mixed solution 2 containing the reaction mixture (1), tetrafluoroethylene and a radical initiator and to add tetrafluoroethylene to the compound (1) thereby to obtain a reaction mixture (2) containing the compound (2) more than the reaction mixture (1); a reactor 16 to prepare a mixed solution 3 containing the reaction mixture (2), tetrafluoroethylene and a radical initiator and to add tetrafluoroethylene to the compound (1) thereby to obtain a reaction mixture (3) containing the compound (2) more than the reaction mixture (2); a reactor 18 to prepare a mixed solution 4 containing the reaction mixture (3), tetrafluoroethylene and a radical initiator and to add tetrafluoroethylene to the compound (1) thereby to obtain a reaction mixture (4) containing the compound (2) more than the reaction mixture (3); a compound (1)-supplying line 20 to supply the compound (1) to the reactor 12; a tetrafluoroethylene-supplying line 22 to supply tetrafluoroethylene to the reactor 12; a radical initiator-supplying line 24 to supply a radical initiator to the reactor 12; a reaction mixture (1)-supplying line 26 to supply the reaction mixture (1) in the reactor 12 to the reactor 14; a tetrafluoroethylene-supplying line 28 to supply tetrafluoroethylene to the reactor 14; a radical initiator-supplying line 30 to supply a radical initiator to the reactor 14; a reaction mixture (2)-supplying line 32 to supply the reaction mixture (2) in the reactor 14 to the reactor 16; a tetrafluoroethylene-supplying line 34 to supply tetrafluoroethylene to the reactor 16; a radical initiator-supplying line 36 to supply a radical initiator to the reactor 16; the reaction mixture (3)-supplying line 38 to supply the reaction mixture (3) in the reactor 16 to the reactor 18; a tetrafluoroethylene-supplying line 40 to supply tetrafluoroethylene to the reactor 18; a radical initiator-supplying line 42 to supply a radical initiator to the reactor 18; and a reaction mixture (4)-discharge line 44 to discharge the reaction mixture (4) from the reactor 18.

Each of the reactors 12, 14, 16 and 18 is an autoclave provided with a stirrer.

Here, the apparatus for producing a fluoroalkyl iodide is not limited to one shown in the FIGURE.

For example, a tubular reactor may be employed as the reactor. The cross-sectional shape of the tubular reactor is not limited to circular, and it may be ellipsoidal or rectangular. The tubular reactor may be of a single tube type. In the tubular reactor, reactor tubes are not necessarily disposed so that the axis directions are in the vertical direction. The tubular reactor may be filled with a filler. The material of the filler is preferably a material having a corrosion resistance, and it may be a metal or a resin. The filler may be an irregular filler or a regular filler.

The reactors may be independent of one another, or may be a plurality of sections divided in a reactor. Further, as the apparatus for producing a fluoroalkyl iodide, the production apparatus described in Patent Document 1 may be employed.

<Process for Producing Fluoroalkyl Iodide>

Now, the process for producing a fluoroalkyl iodide employing the production apparatus 10 will be described.

The process for producing a fluoroalkyl iodide of the present invention comprises the following steps (a) to (d). Further, it preferably has the following step (e).

Step (a): A step of obtaining a mixed solution containing the compound (1), tetrafluoroethylene and a radical initiator.

Step (b): A step of obtaining a reaction mixture (1) containing the compound (2) by the first reaction step of reacting the mixed solution obtained in the step (a).

Step (c): A step of producing a reaction mixture (n) containing the compound (1) and the compound (2) by a total of n reaction steps by repeating (n−1) times (provided that n is an integer of at least 3) a subsequent reaction step of supplying and reacting a radical initiator, or a radical initiator and tetrafluoroethylene, to the reaction mixture (1) obtained in the step (b).

Step (d): A step of separating the compound (2) from the reaction mixture (2) or from the reaction mixture (n) after completion of the n-th reaction step.

Step (e): A step of using the compound (1) as the compound (1) in the first reaction step, after separating the compound (2) from the reaction mixture (2) or the reaction mixture (n).

Step (a):

As a means to mix the compound (1), tetrafluoroethylene and a radical initiator, a reactor having a stirrer, a line mixer or a pump circulation may, for example, be mentioned.

For the mixing of the compound (1), tetrafluoroethylene and the radical initiator, it is preferred to have a step of mixing by means of a stirrer before the reaction, since uniform dispersion increases the selectivity.

The retention time in the step (a) is preferably at most 30 minutes, more preferably at most 20 minutes, particularly preferably from 5 to 20 minutes.

The mixing temperature is preferably a temperature at which the radical initiator will not be decomposed. Specifically, it is preferably from −20 to 100° C.

In the compound (1), $R^f$ is a polyfluoroalkyl group having at most 4 carbon atoms, preferably from 2 to 4 carbon atoms, which may be straight chain-structured or branched, and is preferably a straight chain perfluoroalkyl group. The compound (1) may be selected depending upon the carbon chain length of the desired compound (2). When the desired compound (2) is $C_6F_{13}I$, the compound (1) may be $C_4F_9I$, or a mixture of $C_4F_9I$ and $C_2F_5I$.

The molar ratio of the compound (1) to tetrafluoroethylene (i.e. the compound (1)/tetrafluoroethylene) in the mixed solution, is preferably at least 1. Tetrafluoroethylene will not usually dissolve more than equimolar to the compound (1), and therefore, when the compound (1)/tetrafluoroethylene is at least 1, tetrafluoroethylene will be dissolved in the compound (1) in a concentration of not higher than the saturation concentration, whereby gas-liquid separation is less likely to occur in the step (b). The amount of tetrafluoroethylene to be supplied is from 0.01 to 10 mol %, preferably from 0.05 to 10 mol %, particularly preferably from 0.1 to 5 mol %, to the number of moles of the compound (1).

The radical initiator is preferably a radical initiator having a 10 hour half-life temperature of at most 40° C. When the 10 hour half-life temperature of the radical initiator is at most 40° C., it is possible to obtain the compound (2) at higher selectivity with higher productivity. Further, the 10 hour half-life temperature of the radical initiator is preferably at least −20° C., more preferably from 0 to 40° C. For example, as the radical initiator, various initiators such as a peroxide, an azo compound, etc. may be employed. Specifically, diisopropyl peroxydicarbonate, $(C_2F_5COO)_2$, $(C_4F_9COO)_2$, $(C_6F_{13}COO)_2$ or $(C_8F_{17}COO)_2$ may be mentioned. The radical initiator is particularly preferably a fluorinated peroxide, since it is effective to reduce a byproduct.

The amount of the radical initiator is preferably from 0.0005 to 0.5 mol %, more preferably from 0.001 to 0.1 mol %, particularly preferably from 0.001 to 0.05 mol %, to the compound (1).

The method for supplying the radical initiator and tetrafluoroethylene may be addition all at once or continuous addition.

Step (b):

The first reaction step in the present invention may be carried out simultaneously with the mixing step as the above step (a) or may be carried out independently therefrom. In the first reaction step, tetrafluoroethylene is added to the compound (1) in the mixed solution obtained in the step (a) to obtain the compound (2). The reaction temperature is preferably a temperature higher by at least 10° C., more preferably at least 20° C., than the 10 hour half-life temperature of the radical initiator. At such a temperature, numerous radicals will be generated, whereby the desired compound (2) may be obtained at higher selectivity. Specifically, the reaction temperature is preferably from 40 to 120° C., more preferably from 50 to 100° C., particularly preferably from 50 to 90° C.

The reaction time is preferably a sufficient time for tetrafluoroethylene in the mixed solution to contribute to the reaction and be consumed. Specifically, it is preferably from 5 to 60 minutes, more preferably from 10 to 40 minutes.

In the step (b), in a case where a tubular reactor is employed, it is preferred to carry out a control to prevent gas-liquid separation of the mixed solution. In order to carry out such a control to prevent gas-liquid separation, a method may, for example, be mentioned wherein a fluoroalkyl iodide and tetrafluoroethylene as materials for the reaction are preliminarily made into a homogeneous liquid mixture, which is supplied to the tubular reactor, and while maintaining the reaction system in a liquid phase state under a condition to prevent gas-liquid separation, tetrafluoroethylene supplied into the reactor is consumed substantially in the reactor. In a case where the mixed solution undergoes gas-liquid separation, the gas phase portion to be formed is tetrafluoroethylene which is not dissolved in the mixed solution. Therefore, once a gas phase is formed, tetrafluoroethylene tends to be localized at the liquid phase portion in the vicinity of the interface with the gas phase portion, and the telomerization of the compound (2) with tetrafluoroethylene tends to proceed at the liquid phase portion in the vicinity of the interface, whereby a fluoroalkyl iodide having a chain length longer than the compound (2) is likely to be formed, and the selectivity for the compound (2) tends to decrease. Whereas, when the mixed solution will not undergo gas-liquid separation, tetrafluoroethylene will be present in the mixed solution, and therefore, telomerization of the compound (1) with tetrafluoroethylene will preferentially proceed, whereby a fluoroalkyl iodide having a long chain length is less likely to be formed, and the selectivity for the compound (2) will be improved.

Step (c):

In the second reaction step, a radical initiator, or a radical initiator and tetrafluoroethylene, are supplied and reacted to the reaction mixture (1) obtained in the step (b), whereby it is possible to obtain a reaction mixture (2) having a higher content of the compound (2) than in the reaction mixture (1).

The conversion of the compound (1) in the reaction mixture after completion of the second reaction step is at most 10%, preferably from 1 to 8%, more preferably from 1 to 5%, in order to prevent an increase of the chain length of the desired compound (2). When the conversion of the compound (1) exceeds 10%, the addition reaction of the compound (2) and tetrafluoroethylene will occur, whereby the selectivity will decrease.

Further, by repeating (n−1) times (provided that n is an integer of at least 3) a subsequent reaction step of supplying and reacting a radical initiator, or a radical initiator and tetrafluoroethylene, to the reaction mixture (1) obtained in the step (b), in the subsequent n-th reaction step, it is possible to obtain a reaction mixture (n) having a higher content of the compound (2) than in the reaction mixture (n−1).

The number of repeating times of the subsequent reaction step of supplying and reacting a radical initiator, or a radical initiator and tetrafluoroethylene, to the reaction mixture formed in the preceding reaction step, is preferably at least 3 times, more preferably from 3 to 12 times, particularly preferably from 3 to 8 times. When the number of repeating times of the reaction step, is at least 3, the selectivity for the compound (2) and the productivity will be improved.

Further, in the same manner as in the step (a), it is preferred to have, prior to each reaction step, a step of mixing the compound (1) and/or the compound (2), tetrafluoroethylene and the radical initiator by means of a stirrer.

The conversion of the compound (1) in the reaction mixture after completion of the n-th reaction step, is at most 10%, preferably from 1.6 to 8%, more preferably from 1.8 to 5%, in order to prevent an increase of the chain length more than the desired compound (2). If the conversion of the compound (1) exceeds 10%, an addition reaction of the compound (2) and tetrafluoroethylene will occur, and the selectivity will decrease.

The reaction temperature in each reaction step is preferably from 40 to 120° C., more preferably from 50 to 100° C., particularly preferably from 50 to 90° C.

The reaction time in each reaction step is preferably from 5 to 60 minutes, more preferably from 10 to 40 minutes.

The maximum amount of tetrafluoroethylene present in each reaction step is maintained to be within a range of from 0.01 to 10 mol % to the total number of moles of the compound (1) and the compound (2). Such a range is more preferably from 0.05 to 10 mol %, particularly preferably from 0.1 to 5 mol %. If the maximum amount of tetrafluoroethylene present exceeds 10 mol %, tetrafluoroethylene tends to be more readily react with the formed compound (2), whereby the selectivity tends to decrease. The total amount of tetrafluoroethylene to be supplied is preferably from 0.02 to 10 mol %, more preferably from 0.1 to 10 mol %, particularly preferably from 0.2 to 5 mol %, to the total number of moles of the compound (1) and the compound (2).

In each reaction step, tetrafluoroethylene present in the reactor in such a step may not be all reacted. Unreacted tetrafluoroethylene will be sent, as a component in the reaction mixture, to a reactor of the next reaction step. Accordingly, such unreacted tetrafluoroethylene may be reacted without supplying tetrafluoroethylene to the reactor in the next reaction step. For example, by supplying tetrafluoroethylene to only the reactor in the first reaction step, it is possible to form the compound (2) without supplying tetrafluoroethylene to reactors in the second and subsequent reaction steps.

The maximum amount of tetrafluoroethylene present in each reaction step means the total amount of such unreacted tetrafluoroethylene and tetrafluoroethylene supplied to the reactor in such a reaction step. In such a reaction step, in the period until the initiation of the reaction after supplying tetrafluoroethylene, there is the time when the amount of tetrafluoroethylene present in such a reaction step becomes maximum.

The maximum amount of the radial initiator present in each reaction step is from 0.0005 to 0.5 mol %, more preferably from 0.001 to 0.1 mol %, particularly preferably from 0.001 to 0.05 mol %, to the total number of moles of the compound (1) and the compound (2). It is commonly known that in telomerization, the productivity and selectivity will be improved when the amount of the radical initiator is large. However, an excess radical initiator will lower the efficiency in the use of the initiator, whereby the productivity will decrease.

The total amount of the radical initiator to be supplied is preferably from 0.001 to 0.5 mol %, more preferably from 0.002 to 0.1 mol %, particularly preferably from 0.002 to 0.05 mol %, to the total number of moles of the compound (1) and the compound (2).

In each reaction step, the radical initiator present in the reactor in such a step may not be all reacted. An unreacted radical initiator will be sent to a reactor in the next reaction step as a component in the reaction mixture. Accordingly, such an unreacted radical initiator may be reacted without supplying a radical initiator to the reactor in the next reaction step. In a usual reaction, the amount of an unreacted radical initiator in the reaction mixture is small, and therefore, it is usually preferred to supply a radical initiator in the reactor in each reaction step. The maximum amount of the radical initiator present in each reaction step means the total amount of such an unreacted radical initiator and the radical initiator supplied to the reactor in such a reaction step. In such a reaction step, in the period until the initiation of the reaction after the supplying the radical initiator, there is the time when the amount of the radical initiator present in such a reaction step becomes maximum.

After completion of the step (c), it is possible to obtain the desired compound (2) at high selectivity. For example, in a case where the compound (2) is $C_6F_{13}I$, it is possible to suppress formation of a fluoroalkyl iodide having at least 8 carbon atoms, and (C8+/C6)×100% i.e. the ratio (percentage) of the formed amount (mol) of a fluoroalkyl iodide having at least 8 carbon atoms to the formed amount (mol) of $C_6F_{13}I$, is made to be preferably at most 10%, particularly preferably at most 6%.

In the present invention, (C8+/C6)×100% i.e. the ratio (percentage) of the formed amount (mol) of a fluoroalkyl iodide having at least 8 carbon atoms to the formed amount (mol) of $C_6F_{13}I$, is referred to also as the selectivity for a fluoroalkyl iodide having at least 8 carbon atoms.

In the present invention, it is particularly preferred that the conversion of the fluoroalkyl iodide (1) as the compound (1) is from 1.8 to 5%, and the selectivity for a fluoroalkyl iodide having at least 8 carbon atoms is at most 6%.

Step (d):

In order to separate the compound (2) from the reaction mixture (2) or the reaction mixture (n) after completion of the n-th reaction step, distillation, liquid separation or extraction may, for example, be suitably employed depending upon the particular purpose. It is particularly preferred to separate an unreacted compound (1), the formed compound (2) and byproducts by distilling the reaction mixture (n).

Step (e):

From the viewpoint of the productivity and costs, it is preferred to use the compound (1) as the compound (1) in the first reaction step, after separating the compound (2) from the reaction mixture.

In the present invention, it is preferred to carry out the steps (a) to (e), respectively, in a continuous operation, and it is particularly preferred to carry out the steps (a) to (e) in a continuous process.

In order to further extend the chain length of the compound (2) to obtain a fluoroalkyl iodide having a long carbon chain as a final product, when steps (a) to (e) are regarded as one cycle, the cycle may be repeated by using a compound (2) of each cycle as a compound (1) of the next cycle.

The recovered compound (2) may be employed as e.g. a raw material for an alcohol component of a fluoroalkyl acrylate. The compound (2) is preferably $C_6F_{13}I$ since it has the following merits.

(i) A water/oil repellent agent containing a (co)polymer of the fluoroalkyl acrylate can impart water repellency to a substrate while the texture of the substrate is maintained, and it has good adhesiveness to a substrate at a low temperature (low temperature curing property).

(ii) The fluoroalkyl acrylate has a good emulsification stability at a time of polymerization.

(iii) A fluoroalkyl compound containing at most 6 carbon atoms has better environmental friendliness such as biodegradability as compared with fluoroalkyl compounds containing at least 8 carbon atoms.

A fluoroalkyl acrylate can be produced by a known process.

The fluoroalkyl acrylate obtainable may, for example, be a compound (A), preferably a compound (A-1).

Here, Z is H, $CH_3$, $C_2H_5$, Cl, F or Br, and y is an integer of at least 1.

In the process for producing a fluoroalkyl iodide of the present invention described above, by repeating two or more reaction steps, it is possible to obtain a compound (2) with high selectivity and high productivity.

That is, by controlling the maximum amount of tetrafluoroethylene present in each reaction step to be low, it is possible to prevent the compound (1) and tetrafluoroethylene from reacting repeatedly thereby to increase the selectivity for a polymerization degree. Further, by controlling the maximum amount of the radical initiator present to be low, it is possible to prevent a mutual reaction of formed radicals to one another thereby to increase the reaction efficiency and the productivity.

EXAMPLES

Now, the present invention will be described in detail with reference to Examples, but the present invention is by no means limited to these Examples.

Examples 1 to 5 and 10 to 12 are Examples of the present invention, and Examples 6 to 9, 13 and 14 are Comparative Examples.

With respect to a mixed solution discharged from a reactor, a composition analysis was carried out by a gas chromatograph, to obtain C8+/C6(%) and the $C_4F_9I$ conversion by the following methods.

<C8+/C6(%)>

Using the result of the composition analysis, C8+/C6(%) was obtained by the following formula.

C8+/C6(%)=($C_8F_{17}I$ (mol)+$C_{10}F_{21}I$ (mol)+ ... )/
$C_6F_{13}I$ (mol)×100

<$C_4F_9I$ Conversion>

Using the reactor outlet flow rate values and the results of the composition analysis, the $C_4F_9I$ conversion was obtained by the following formula.

$C_4F_9I$ conversion(%)=[1−{$C_4F_9I$ outlet concentration (g/g)×outlet flow rate (g/min)}/{$C_4F_9I$ inlet concentration (g/g)×inlet flow rate (g/min)}]×100

Example 1

Into an autoclave 1 (made of stainless steel, capacity: 1 L) having a stirrer, $C_4F_9I$ as the compound (1) was supplied at a flow rate of 25 mL/min, $CF_2$=$CF_2$ (tetrafluoroethylene) was supplied at a flow rate of 0.10 g/min, and $(C_2F_5COO)_2$ (10 hour half-life temperature: 28° C.) was supplied at a flow rate of 0.0065 mmol/min, and they were mixed by the stirrer to prepare a mixed solution. The temperature in the autoclave was set to be 70° C., and the retention time of the mixed solution in the autoclave was set to be 20 minutes. The obtained reaction mixture (1) contained $C_6F_{13}I$ as the compound (2). The amounts of tetrafluoroethylene and $(C_2F_5COO)_2$ were 0.65 mol % and 0.00425 mol %, respectively, to $C_4F_9I$.

From the bottom of the autoclave 1, the reaction mixture (1) was withdrawn and supplied into an autoclave 2 (made of stainless steel, capacity: 1 L) having a stirrer, at a flow rate of 25 mL/min, $CF_2=CF_2$ (tetrafluoroethylene) was supplied at a flow rate of 0.10 g/min, and $(C_2F_5COO)_2$ (10 hour half-life temperature: 28° C.) was supplied at a flow rate of 0.0065 mmol/min, and they were mixed by the stirrer to prepare a mixed solution. The temperature in the autoclave was set to be 70° C., and the retention time of the mixed solution in the autoclave was set to be 20 minutes to obtain a reaction mixture (2) containing $C_6F_{13}I$ as the compound (2). The amounts of tetrafluoroethylene and $(C_2F_5COO)_2$ supplied, were 0.65 mol % and 0.00425 mol %, respectively, to the total of telomers in the mixed solution.

From the bottom of the autoclave 2, the reaction mixture (2) was withdrawn, and an analysis of the composition was carried out to obtain the $C_4F_9I$ conversion and C8+/C6(%). The results are shown in Table 1.

Examples 2 to 5

A reaction mixture (n) containing $C_6F_{13}I$ was produced in the same manner as in Example 1 except that the number (n) of repeated reaction steps and the amounts of tetrafluoroethylene and $(C_2F_5COO)_2$ supplied in each reaction step were changed as shown in Table 1. As the reactor in the third or subsequent reaction step, the same autoclave having a stirrer as the autoclave 2 in Example 1 was used, and other than the reaction conditions shown in Table 1, the reaction was carried out under the same conditions as the reaction in the second reaction step in Example 1.

With respect to the reaction mixture (n) discharged from the reactor in the final step, analysis of the composition was carried out to obtain C8+/C6(%) and the $C_4F_9I$ conversion. The results are shown in Table 1.

Example 6

Into an autoclave 1 (made of stainless steel, capacity: 1 L) having a stirrer, $C_4F_{91}$ was supplied at a flow rate of 25 mL/min, $CF_2=CF_2$ (tetrafluoroethylene) was supplied at a flow rate of 0.20 g/min, and $(C_2F_5COO)_2$ (10 hour half-life temperature: 31° C.) was supplied at a flow rate of 0.013 mmol/min, and they were mixed by the stirrer to prepare a mixed solution. The temperature in the autoclave was set to be 70° C., and the retention time of the mixed solution in the autoclave was set to be 20 minutes. The amounts of tetrafluoroethylene and $(C_2F_5COO)_2$ were 1.30 mol % and 0.0085 mol %, respectively, to the total of telomers in the mixed solution.

From the bottom of the autoclave 1, the reaction mixture was withdrawn, and an analysis of the composition was carried out to obtain the $C_4F_9I$ conversion and C8+/C6(%). The results are shown in Table 1.

Examples 7 to 9

A reaction mixture containing $C_6F_{13}I$ was produced in the same manner as in Example 6 except that the amounts of tetrafluoroethylene and $(C_2F_5COO)_2$ supplied were changed to the amounts shown in Table 1.

With respect to the reaction mixture discharged from the bottom of the autoclave 1, analysis of the composition was carried out to obtain the $C_4F_9I$ conversion and C8+/C6(%). The results are shown in Table 1.

Example 10

Into an autoclave 1 (made of stainless steel, capacity: 1 L) having a stirrer, as a mixing vessel, $C_4F_9I$ was supplied at a flow rate of 25 mL/min, $CF_2=CF_2$ (tetrafluoroethylene) was supplied at a flow rate of 0.20 g/min, and $(C_2F_5COO)_2$ (10 hour half-life temperature: 28° C.) was supplied at a flow rate of 0.013 mmol/min, and they were mixed by the stirrer to prepare a mixed solution. The temperature in the autoclave 1 was set to be 10° C., and the retention time of the mixed solution in the autoclave 1 was set to be 10 minutes. The amounts of tetrafluoroethylene and $(C_2F_5COO)_2$ supplied, were 1.30 mol % and 0.0085 mol %, respectively, to $C_4F_9I$.

From the bottom of the autoclave 1, only the mixed solution was withdrawn in a state free from a gas phase portion, and the mixed solution was supplied to the bottom of a tubular reactor 1 (single tube type, capacity: 0.5 L).

The mixed solution was flown from the inlet of the reactor tube in the tubular reactor 1 to its outlet so that the mixed solution underwent no gas-liquid separation, to obtain a reaction mixture (1) containing $C_6F_{13}I$ as the compound (2). The temperature in the reactor tube was set to be 70° C., and the retention time of the mixed solution in the tubular reactor 1 was set to be 20 minutes.

From the tubular reactor 1, the reaction mixture (1) was withdrawn and supplied to an autoclave 2 (made of stainless steel, capacity: 1 L) having a stirrer, and $C_4F_9I$ was supplied at a flow rate of 25 mL/min, $CF_2=CF_2$ (tetrafluoroethylene) was supplied at a flow rate of 0.16 g/min, and $(C_2F_5COO)_2$ (10 hour half-life temperature: 28° C.) was supplied at a flow rate of 0.013 mmol/min, and they were mixed by the stirrer to prepare a mixed solution. The temperature in the autoclave 2 was set to be 10° C., and the retention time of the mixed solution in the autoclave 2 was set to be 10 minutes. The amounts of tetrafluoroethylene and $(C_2F_5COO)_2$ supplied, were 1.02 mol % and 0.0085 mol %, respectively, to $C_4F_9I$.

From the bottom of the autoclave 2, only the mixed solution was withdrawn in a state free from a gas phase portion, and the mixed solution was supplied to the bottom of a tubular reactor 2 (single tube type, capacity: 0.5 L).

The mixed solution was flown from the inlet of the reactor tube in the tubular reactor 2 to its outlet so that the mixed solution underwent no gas-liquid separation, to obtain a reaction mixture (2) containing $C_6F_{13}I$ as the compound (2). The temperature in the reactor tube was set to be 70° C., and the retention time of the mixed solution in the tubular reactor 2 was set to be 20 minutes.

From the outlet of the tubular reactor 2, the reaction mixture was withdrawn, and analysis of the composition was carried out to obtain the $C_4F_9I$ conversion and C8+/C6(%). The results are shown in Table 2.

Examples 11 and 12

A reaction mixture (n) containing $C_6F_{13}I$ was obtained in the same manner as in Example 4 except that the number (n) of repeated reaction steps and the amounts of tetrafluoroethylene and $(C_2F_5COO)_2$ supplied to the autoclave having a stirrer in each reaction step were changed as shown in Table 2.

With respect to the reaction mixture (n) discharged from the tubular reactor, analysis of the composition was carried out to obtain the $C_4F_9I$ conversion and C8+/C6(%). The results are shown in Table 2.

Example 13

Into an autoclave (made of stainless steel, capacity: 1 L) having a stirrer, as a mixing vessel, $C_4F_9I$ was supplied at a flow rate of 25 mL/min, $CF_2\!\!=\!\!CF_2$ (tetrafluoroethylene) was supplied at a flow rate of 0.36 g/min, and $(C_2F_5COO)_2$ (10 hour half-life temperature: 28° C.) was supplied at a flow rate of 0.026 mmol/min, and they were mixed by the stirrer to prepare a mixed solution. The temperature in the autoclave was set to be 10° C., and the retention time of the mixed solution in the autoclave was set to be 10 minutes. The amounts of tetrafluoroethylene and $(C_2F_5COO)_2$ supplied, were 2.32 mol % and 0.017 mol %, respectively, to $C_4F_9I$.

From the bottom of the autoclave, only the mixed solution was withdrawn in a state free from a gas phase portion, and the mixed solution was supplied to the bottom of a tubular reactor (single tube type, capacity: 0.5 L).

The mixed solution was flown from the inlet of the reactor tube in the tubular reactor to its outlet so that the mixed solution underwent no gas-liquid separation, to obtain a reaction mixture containing $C_6F_{13}I$ as the compound (3). The temperature in the reactor tube was set to be 70° C., and the retention time of the mixed solution in the tubular reactor was set to be 20 minutes.

With respect to the reaction mixture discharged from the tubular reactor, analysis of the composition was carried out to obtain the $C_4F_9I$ conversion and C8+/C6(%). The results are shown in Table 2.

Example 14

A reaction mixture containing $C_6F_{13}I$ was obtained in the same manner as in Example 13 except that the amounts of tetrafluoroethylene and $(C_2F_5COO)_2$ supplied to the autoclave having a stirrer were changed to the amounts shown in Table 2.

With respect to the reaction mixture discharged from the tubular reactor, analysis of the composition was carried out to obtain the $C_4F_9I$ conversion and C8+/C6(%). The results are shown in Table 2.

TABLE 1

|  | Ex. 1 | Ex. 2 | Ex. 3 | Ex. 4 | Ex. 5 | Ex. 6 | Ex. 7 | Ex. 8 | Ex. 9 |
| --- | --- | --- | --- | --- | --- | --- | --- | --- | --- |
| Number (n) of reaction steps | 2 | 2 | 4 | 4 | 4 | All at once | All at once | All at once | All at once |
| Amount of 4F supplied in first step (g/min) | 0.1 | 0.2 | 0.1 | 0.1 | 0.17 | — | — | — | — |
| Amount of 4F supplied in second or subsequent step (g/min) | 0.1 | 0.2 | 0.1 | 0.1 | 0.17 | — | — | — | — |
| Total amount of 4F supplied (g/min) (mol %) | 0.20 1.30 | 0.40 2.57 | 0.40 2.57 | 0.40 2.57 | 0.68 4.29 | 0.20 1.30 | 0.36 2.32 | 0.36 2.32 | 0.72 4.53 |
| Amount of initiator supplied in each step (mol %) | 0.00425 | 0.0085 | 0.00425 | 0.0085 | 0.0085 | — | — | — | — |
| Total amount of initiator supplied (mol %) | 0.0085 | 0.017 | 0.017 | 0.034 | 0.034 | 0.0085 | 0.017 | 0.0703 | 0.0703 |
| C4 conversion (conv. %) | 1.01 | 1.94 | 2.42 | 2.66 | 4.99 | 0.78 | 1.52 | 1.55 | 3.22 |
| C8+/C6 (%) | 2.3 | 4.3 | 3.3 | 3.1 | 5.7 | 3 | 4.8 | 3.8 | 7.6 |

TABLE 2

|  | Ex. 10 | Ex. 11 | Ex. 12 | Ex. 13 | Ex. 14 |
| --- | --- | --- | --- | --- | --- |
| Number of reactions | 2 | 4 | 6 | All at once | All at once |
| Amount of 4F supplied in first step (g/min) | 0.2 | 0.2 | 0.2 | — | — |
| Amount of 4F supplied in second or subsequent step (g/min) | 0.16 | 0.15 | 0.1 | — | — |
| Total amount of 4F supplied (g/min) (mol %) | 0.36 2.32 | 0.65 4.11 | 0.60 3.80 | 0.36 2.32 | 0.72 4.53 |
| Amount of initiator supplied in each step (mol %) | 0.0085 | 0.0085 | 0.0085 | — | — |
| Total amount of initiator supplied (mol %) | 0.017 | 0.034 | 0.051 | 0.017 | 0.329 |
| C4 (conv. %) | 2.23 | 3.87 | 4.21 | 1.81 | 4.9 |
| C8+/C6 (%) | 4.4 | 5.4 | 4.4 | 6.5 | 11.8 |

INDUSTRIAL APPLICABILITY

A fluoroalkyl iodide obtained by the process of the present invention is useful as a raw material for a water/oil repellent or a fluorinated surfactant.

This application is a continuation of PCT Application No. PCT/JP2011/062732, filed on Jun. 2, 2011, which is based upon and claims the benefit of priority from Japanese Patent Application No. 2010-129013 filed on Jun. 4, 2010. The contents of those applications are incorporated herein by reference in its entirety.

| REFERENCE SYMBOLS | |
|---|---|
| 10: | Schematic view of an apparatus for producing a fluoroalkyl iodide |
| 20: | Compound (1)-supplying line |
| 12, 14, 16, 18: | Autoclave having a stirrer, as a reactor |
| 22, 28, 34, 40: | Tetrafluoroethylene-supplying line |
| 24, 30, 36, 42: | Radial initiator-supplying line |
| 26, 32, 38, 44: | Reaction mixture (n)-supplying line |

What is claimed is:

1. A process for producing a fluoroalkyl iodide (2) represented by formula (2), comprising:
    a first reaction step of supplying and reacting tetrafluoroethylene and a radical initiator to a fluoroalkyl iodide (1) represented by formula (1), to thereby form a reaction mixture (1), followed by
    a second reaction step of supplying and reacting a radical initiator, or a radical initiator and tetrafluoroethylene, to the reaction mixture (1) formed in the first reaction step, to thereby form a reaction mixture (2) comprising the fluoroalkyl iodide (1) represented by formula (1) and the fluoroalkyl iodide (2) represented by formula (2):

$$R^f I \quad (1)$$

$$R^f CF_2 CF_2 I \quad (2)$$

wherein
$R^f$ is a fluoroalkyl group having at most 4 carbon atoms,
the maximum amount of tetrafluoroethylene present in each reaction step is maintained to be within a range of from 0.01 to 10 mol % to the total number of moles of the fluoroalkyl iodide (1) and the fluoroalkyl iodide (2),
the maximum amount of the radical initiator present in each reaction step is adjusted to be from 0.0005 to 0.5 mol % to the total number of moles of the fluoroalkyl iodide (1) and the fluoroalkyl iodide (2), and
the conversion of the fluoroalkyl iodide (1) in the reaction mixture (2) after completion of the second reaction step is adjusted to be at most 10%.

2. The process according to claim 1, which has, prior to each reaction step, a step of mixing the fluoroalkyl iodide (1) and/or the fluoroalkyl iodide (2), tetrafluoroethylene and the radical initiator by a stirrer.

3. The process according to claim 1, which has a step (d) of separating the fluoroalkyl iodide (2) from the reaction mixture (2).

4. The process according to claim 1, wherein the reaction temperature in each reaction step is from 40 to 120° C.

5. The process according to claim 1, wherein after separating the fluoroalkyl iodide (2) from the reaction mixture (2), the fluoroalkyl iodide (1) is used as the fluoroalkyl iodide in the reaction step (1).

6. The process according to claim 1, wherein the fluoroalkyl iodide (1) is $C_4F_9I$, or a mixture of $C_4F_9I$ and $C_2F_5I$.

7. The process according to claim 1, wherein the fluoroalkyl iodide (2) is $C_6F_{13}I$.

8. The process according to claim 1, wherein the radical initiator is a fluorinated peroxide.

9. The process according to claim 1, wherein the conversion of the fluoroalkyl iodide (1) is from 1.8 to 5%, and the selectivity for a fluoroalkyl iodide having at least 8 carbon atoms is at most 6%.

10. A process for producing a fluoroalkyl iodide (2) represented by formula (2), comprising:
    a first reaction step of supplying and reacting tetrafluoroethylene and a radical initiator to a fluoroalkyl iodide (1) represented by formula (1), to thereby form a reaction mixture (n−1), followed by
    a total of n reaction steps by repeating (n−1) times (provided that n is an integer of at least 3) a subsequent reaction step of supplying and reacting a radical initiator, or a radical initiator and tetrafluoroethylene, to the reaction mixture (n−1) formed in the preceding reaction step, to thereby form a reaction mixture (n) comprising the fluoroalkyl iodide (1) represented by formula (1) and the fluoroalkyl iodide (2) represented by formula (2)

$$R^f I \quad (1)$$

$$R^f CF_2 CF_2 I \quad (2)$$

wherein
$R^f$ is a fluoroalkyl group having at most 4 carbon atoms,
the maximum amount of tetrafluoroethylene present in each reaction step is maintained to be within a range of from 0.01 to 10 mol % to the total number of moles of the fluoroalkyl iodide (1) and the fluoroalkyl iodide (2),
the maximum amount of the radical initiator present in each reaction step is adjusted to be from 0.0005 to 0.5 mol % to the total number of moles of the fluoroalkyl iodide (1) and the fluoroalkyl iodide (2), and
the conversion of the fluoroalkyl iodide (1) in the reaction mixture (n) after completion of the n-th reaction step is adjusted to be at most 10%.

11. The process according to claim 10, which has, prior to each reaction step, a step of mixing the fluoroalkyl iodide (1) and/or the fluoroalkyl iodide (2), tetrafluoroethylene and the radical initiator by a stirrer.

12. The process according to claim 10, which has a step (d) of separating the fluoroalkyl iodide (2) from the reaction mixture (n) after completion of the n-th reaction step.

13. The process according to claim 10, wherein the reaction temperature in each reaction step is from 40 to 120° C.

14. The process according to claim 10, wherein after separating the fluoroalkyl iodide (2) from the reaction mixture (n), the fluoroalkyl iodide (1) is used as the fluoroalkyl iodide in the reaction step (1).

15. The process according to claim 10, wherein the fluoroalkyl iodide (1) is $C_4F_9I$, or a mixture of $C_4F_9I$ and $C_2F_5I$.

16. The process according to claim 10, wherein the fluoroalkyl iodide (2) is $C_6F_{13}I$.

17. The process according to claim 10, wherein the radical initiator is a fluorinated peroxide.

18. The process according to claim 10, wherein the conversion of the fluoroalkyl iodide (1) is from 1.8 to 5%, and the selectivity for a fluoroalkyl iodide having at least 8 carbon atoms is at most 6%.

* * * * *